United States Patent [19]
Kim et al.

[11] Patent Number: 5,633,155
[45] Date of Patent: May 27, 1997

[54] EXPRESSION VECTOR FOR PHYTOLACCA ANTIVIRAL PROTEIN AND PROCESS FOR PREPARING TRANSGENIC PLANT TRANSFORMED THEREWITH

[75] Inventors: Man-Keun Kim; Kwan-Ho Lee, both of Seoul; Byeong-Kook Na, Incheon; Han-Seung Jeong; Kyu-Whan Choi, both of Seoul; Young-Ho Moon, Kuri; Hong-Seob Jeon, Seoul, all of Rep. of Korea

[73] Assignee: Jinro Limited, Seoul, Rep. of Korea

[21] Appl. No.: 373,858

[22] Filed: Jan. 18, 1995

Related U.S. Application Data

[63] Continuation-in-part of Ser. No. 49,075, Apr. 20, 1993, abandoned.

[30] Foreign Application Priority Data

Aug. 19, 1992 [KR] Rep. of Korea ............... 92-14895

[51] Int. Cl.$^6$ ............... C12N 1/00; C12N 15/09; C12N 15/29; C12N 15/82

[52] U.S. Cl. ............... 435/172.3; 435/69.1; 435/252.3; 536/23.6; 800/205

[58] Field of Search ............... 435/172.3, 69.1, 435/240.4, 240.49, 252.3; 536/23.6; 935/9; 800/205

[56] References Cited

PUBLICATIONS

Looge et al. (1993, Aug.) Proc. Natl Acad Sci USA 90:7089–7093.
Lin et al (1991) Plant Molec. Biol. 17:609–614.

*Primary Examiner*—Douglas W. Robinson
*Assistant Examiner*—Elizabeth F. McElwain
*Attorney, Agent, or Firm*—Darby & Darby

[57] ABSTRACT

The present invention provides a recombinant vector for phytolacca antiviral protein isolated from *Phytolacca americana* L. and a process for preparing transgenic plants transformed therewith. The transgenic plants of the invention were properly transformed with the recombinant vector; PAP was expressed from the transgenic plants in a successful manner; and, virus proliferation was efficiently inhibited by the expressed PAP in the transgenic plants.

2 Claims, 13 Drawing Sheets

FIG. IA

```
1    GAGGAGAGAG AACTAGTTAG TAGGAAGGGA AGATGAAGTC GATGCTTGTG GTGACAATAT
                                              M  K  S    M  L  V    V  T  I  S

61   CAATATGGCT CATTCTTGCA CCAACTTCAA CTTGGGCTGT GAATACAATC ATCTACAATG
     I  W  L    I  L  A    P  T  S  T  W  A  V    N  T  J    J  Y  N  V

121  TTGGAAGTAC CACCATTAGC AAATACGCCA CTTTTCTGAA CAATGCTGCC TGATCTTCGT AATGAAGCGA
     G  S  T    T  I  S    K  Y  A  T  F  L  N    D  L  R    N  E  A  K

181  AAGATCCAAG TTTAAATGC TATGGAATAC CAAGGTTCAA ATAAAAAAC CAATACAAAT ACAAATCCAA
     D  P  S    L  K  C    Y  G  I  P  M  L  P    N  T  N    T  N  P  K

241  AGTACGTGTT GGTTGAGCTC CAAGGTTCAA ATCCCTTTGA CATCACACTA ATGCTGAGAC
     Y  V  L    V  E  L    Q  G  S  N  K  K  T    I  T  L    M  L  R  R

301  GAAACAATTT GTATGTGATG GGTTATTCTG AACCAATAAA TGTCGTTACC
     N  N  L    Y  V  M    G  Y  S  D  P  F  E    T  N  K    C  R  Y  H

361  ATATCTTTAA TGATATCTCA GGTACTGAAC GCCAAGATGT AGAGACTACT CTTTGCCCAA
     I  F  N    D  I  S    G  T  E  R  Q  D  V    E  T  T    L  C  P  N
```

```
421  ATGCCAATTC TCGTGTTAGT AAAAACATAA ACTTTGATAG TCGATATCCA ACATTGGAAT
      A  N  S    R  V  S    K  N  I  N    F  D  S    R  Y  P    T  L  E  S

481  CAAAAGCGGG AGTAAAAATCA AGAAGTCAAG TCCAACTGGG AATTCAAATA CTCGACAGTA
      K  A  G    V  K  S    R  S  Q  V    Q  L  G    I  Q  I    L  D  S  N

541  ATATTGGAAA GATTTCTGGA GTGATGTCAT TCAGAGGCAG AACCGAAGCC GAATTCCTAT
      I  G  K    I  S  G    V  M  S  F    T  E  K    T  E  A    E  F  L  L

601  TGGTAGCCAT ACAAATGGTA TCAGAGGCAG CAAGATTCAA GTACATAGAG AATCAGGTGA
      V  A  I    Q  M  V    S  E  A  A    R  F  K    Y  I  E    N  Q  V  K

661  AAACTAATTT TAACAGAGCA TTCAACCCTA ATCCCAAAGT ACTTAATTTG CAAGAGACAT
      T  N  F    N  R  A    F  N  P  N    P  K  V    L  N  L    Q  E  T  W

721  GGGGTAAGAT TTCAACAGCA ATTCATGATG CCAAGAATGG AGTTTTACCC AAACCTCTCG
      G  K  I    S  T  A    I  H  D  A    K  N  G    V  L  P    K  P  L  E
```

FIG. IC

```
781   AGCTAGTGGA TGCCAGTGGT GCCAAGTGGA TAGTGTTGAG AGTGGATGAA ATCAAGCCTG
       L  V  D    A  S  G    A  K  W  I    V  L  R    V  D  E    I  K  P  D

841   ATGTAGCACT CTTAAACTAC GTTGGTGGGA GCTGTCAGAC AACTTATAAC CAAAATGCCA
       V  A  L    L  N  Y    V  G  G  S    C  Q  T    T  Y  N    Q  N  A  M

901   TGTTTCCTCA ACTTATAATG TCTACTTATT ATAATTACAT GGTTAATCTT GGTGATCTAT
       F  P  Q    L  I  M    S  T  Y  Y    N  Y  M    V  N  L    G  D  L  F

961   TTGAAGGATT CTGATCATAA ACTTAATAAG GAGTATATAT ATATTACTCC AACTATATTA
       E  G  F

1021  TAAAGCTTAA ATAAGAGGCC GTGTTAATTA GTACTTGTTG CCTTTTGCTT TATGGTGTTG

1081  TTTATTATGC CTTGTATGCT TGTAATATTA TCTAGAGAAC AAGATGTACT GTGTAATAGT

1141  CTTGTTTGAA ATAAAACTTC CAATTATGAT GCAAAAAAAA AAAAAAAAAA AAAAA
```

EXPRESSION VECTOR FOR PHYTOLACCA ANTIVIRAL PROTEIN AND PROCESS FOR PREPARING TRANSGENIC PLANT TRANSFORMED THEREWITH

This is a continuation-in-part application of U.S. patent application Ser. No. 08/049,075, filed on Apr. 20, 1993, now abandoned.

FIELD OF THE INVENTION

The present invention relates to an expression vector for antiviral protein, more specifically, a recombinant expression vector for phytolacca antiviral protein isolated from *Phytolacca americana* L. and a process for preparing transgenic plants transformed therewith.

BACKGROUND OF THE INVENTION

Since plants can not escape from applied pathogens because of their immobility, they must be able to defend themselves against the pathogenic challenge by direct or indirect response; and, most plants appear to undertake some general defense mechanism to protect themselves from the applied pathogens, e.g., fungi, bacteria and virus.

In this connection, crude extract isolated from *Phytolacca americana* L. has been reported to inhibit in vivo polypeptide synthesis(see: Owens, R. A. et al., Virology, 56:390–393 (1973)); and, said report has accelerated studies on the phytolacca antiviral protein("PAP") isolated from *Phytolacca americana* L. Under these circumstances, PAPs such as PAP-I and PAP-II produced in spring and summer, respectively, and PAP-S produced from seed, have been discovered and isolated since the early 1970's(see: Irvin, J. D. et al., Arch. Biochem. Biophys., 169:522–528(1975); Irvin, J. D. et al., Arch. Biochem. Biophys., 200:418–425 (1980); Barbieri, I. et al., Biochem. J., 203:55–59(1982)).

On the other hand, as a result of extensive studies on the PAP at the molecular level, it was determined that PAPs inactivate the 60S ribosomal subunit of eucaryotic polypeptide synthesis machinery, which is a general phenomenon as other ribosome-inactivating proteins(RIPs) inactivate said subunit (see: Houston, L. L. et al., J. Biol. Chem., 258:9601–9604 (1983)). Further, it has been reported that: PAP is synthesized and secreted from the cytosol and involved in the control of pathogenic virus; however, the detailed mechanism of virus inactivation has not been proved(see: Ready, M. P. et al., Proc. Natl. Acad. Sci., USA, 83:5053–5056(1986)).

Recently, structure and base sequence of PAP genome, a multigene family, have also been characterized and determined (see: Lin, Q. et al., Plant Mol. Biol., 17:609–614 (1991)); and, therefore, efforts have continued to exist in the art, for the development of expression vectors for PAP and transgenic plants transformed therewith.

SUMMARY OF THE INVENTION

In accordance with the present invention, it has been discovered that: PAP is efficiently produced in transgenic plants transformed with a recombinant PAP expression vector, whereby the transgenic plants have broad-spectrum of viral resistance against diverse pathogenic viruses.

A primary object of the present invention is, therefore, to provide a novel recombinant vector containing PAP gene isolated from cDNA library of *Phytolacca americana* L.

Other object of the present invention is to provide a process for preparing virus-resistant transgenic plants transformed with said recombinant vector.

BRIEF DESCRIPTION OF DRAWINGS

The above and the other objects and features of the present invention will become apparent from the following description given in conjunction with the accompanying drawings, in which:

FIGS. 1A through 1C, when joined at respective match lines A—A and B—B, is the full nucleotide sequence(SEQ ID NO:1) of the PAP gene and amino acid sequence(SEQ ID NO:2) translated therefrom;

DETAILED DESCRIPTION OF THE INVENTION

Figure 2A:
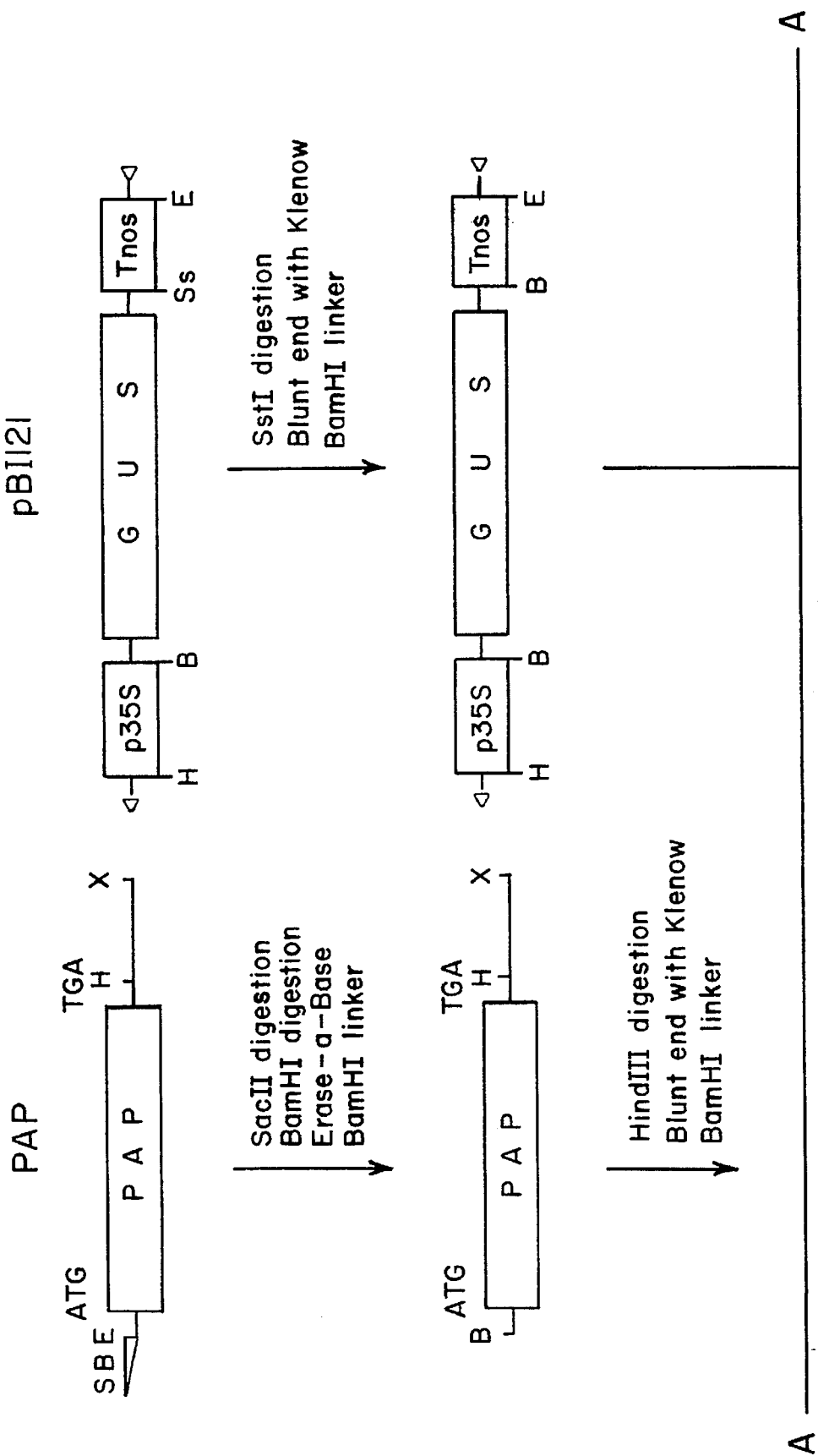
FIGS. 2A and 2B, when joined at match line A—A, are a stepwise construction scheme of expression vector pJRM100.

The present inventors developed a recombinant expression vector pJRM100 containing PAP gene isolated from a cDNA library of *Phytolacca americana* L. and transgenic plants transformed therewith by employing a mediator, *Agrobacterium tumefaciens*.

To isolate PAP gene, the inventors purified total cellular mRNA from leaves of *Phytolacca americana* L. obtained in Korea and constructed cDNA library therefrom. PAP gene was selected by an immunoscreening method employing anti-PAP antibody; and, deletion mutant was prepared from the isolated PAP gene using Erase-a-Base system. DNA sequence of PAP gene was determined in accordance with Sanger's dideoxy chain termination method.

For the preparation of expression vector containing the isolated PAP gene, the 5' site of PAP gene was deleted upto the site of translational initiation(i.e., ATG) and ligated to BamHI linker; and, the 3' site was cleaved with HindIII, treated with Klenow's fragment and ligated to BamHI linker. A recombinant DNA pJRM100 for the expression of PAP was constructed by ligating BamHI fragment of PAP cDNA to a binary vector pBI121(Clonetech, Lot #6019-2, USA).

Agrobacterium tumefaciens LBA 4404, a mediator for plant cell transformation, was transformed with the pJRM100 and transgenic plants were prepared by transforming with said organism. Shoots were induced from the transgenic plant cell on MS selective medium containing 100 mg/l kanamycin and 500 mg/l carbenicillin; and root was generated from said shoots. The plant thus obtained was transferred to pot for continuous growth. Proper insertion of PAP gene to the genome of transgenic plant was identified by Southern blot analysis and its transcription was also verified. Expression of PAP gene in transgenic plants was determined by immunodiffusion assay employing anti-PAP antibody or Western blot analysis. Resistance of transgenic plants to diverse viruses was tested by local lesion assay or ELISA method. The results demonstrated that: transgenic plants were properly transformed with the recombinant vector; PAP was expressed from the transgenic plants in a successful manner; and, virus proliferation was efficiently inhibited by the recombinant PAP expressed in the transgenic plants.

In accordance with the present invention, a recombinant expression vector for PAP made a grant of viral resistance to transgenic plants transformed therewith, grounded on the production of the recombinant PAP.

The present invention is further illustrated by the following examples, which should not be taken to limit the scope of the invention.

EXAMPLE 1

Isolation of PAP Gene

To isolate PAP gene from cDNA library of Phytolacca americana L., anti-PAP antibody was prepared as follows: PAP was purified in accordance with Irvin's method(see: J. D. Irvin, et al., Arch. Biochem. Biophys., 169: 522–528 (1975)). 480 µg of the purified PAP was dissolved in phosphate buffered saline (PBS) solution and combined with Freund's complete adjuvant by a ratio of 1:1(v/v), and the mixture thereof was administrated to a rabbit(~3 kg of body weight) intramuscularly. After 3 weeks, anti-PAP antibody was produced in blood collected from the rabbit. 750 µg of the purified PAP was combined with Freund's incomplete adjuvant by a ratio of 1:1(v/v) for boosting; and, plasma fraction was isolated from the collected blood after 1 week. Then, Protein-A agarose column chromatography was employed to isolate antiserum. Immunodiffusion assay and electrophoresis techniques were employed to determine anti-PAP antibody formation and homogeniety of isolated anti-PAP antibody, respectively. Purified anti-PAP antibody was stored at −70° C. and employed to isolate PAP gene from a cDNA library.

To isolate mRNA from the leaves of Phytolacca americana L., the leaf tissue was homogenized using liquid nitrogen and, to the homogenate thus prepared was added buffer solution for RNA isolation. Total cellular RNA was isolated from supernatant by LiCl sedimentation. mRNA was isolated from the total RNA using oligo(dT) cellulose column chromatography, and the isolated mRNA was employed for DNA synthesis.

A 1st strand DNA was synthesized from template mRNA by M-MuLV reverse transcriptase; and, 2nd strand DNA synthesis by E. coli DNA polymerase followed. Synthesized cDNA linked to EcoRI adaptor, was subject to fractionation by Sephacryl S-400 spun column. Fractionated cDNA was ligated to Uni-Zap XR vector (Stratagene, UK), and in vitro packaging using packaging extract followed.

Immunodiffusion assay employing anti-PAP antibody was carried out to isolate PAP gene from the cDNA library thus prepared. Competent E. coli XL1-Blue was infected with the phage on petri dish, to form plaque of $2 \times 10^4$ pfu. Said bacteria was incubated at 37° C. for 15 min, and incubation at 42° C. for 3.5 hours followed after plating with 3 ml of top agarose. Then, the plate was covered with Hybond-N+ (Amersham, UK) and incubated for 5 hours. Hybond-N+ was blocked with bovine serum albumin and 5 µg/ml of anti-PAP antibody was added. After removal of free anti-PAP antibody which was not bound with PAP, peroxidase conjugated 2nd antibody was reacted with anti-PAP antibody; and, antigen-antibody complexes thus formed were detected by chloronaphthol treatment.

A 2nd immunoscreening procedure was performed with 15 clones obtained from the 1st immunoscreening method, in a similar fashion as above, except that plaque number was $5 \times 10^3$ pfu. A 3rd immunoscreening procedure was carried out with the clones obtained from the 2nd immunoscreening, and 8 plaques isolated therefrom were subject to further experiments.

For the transfer of phagemids of 8 recombinant Uni-Zap XR phages obtained from the 3rd immunoscreening method into E. coli XL1-Blue, in vivo excision technique employing R408 helper phage was carried out. Plasmids were isolated from the 4 colonies thus selected by alkali denaturation method(see: Maniatis et al., Molecular Cloning: A Laboratory Manual, pp 368–369, Cold Spring Harbor Laboratory (1982)), and colonies harboring PAP gene were screened by digesting the isolated plasmids with several restriction enzymes.

EXAMPLE 2

Sequence Determination of PAP Gene

Of the clones harboring PAP gene, plasmids from 2 clones were isolated, and PAP cDNA was sequenced by Sanger's dideoxy chain termination method(see: Sanger, F., Science, 214:1205–1210(1981)). To determine the full nucleotide sequence of PAP gene, DNA was purified from the clones harboring PAP gene. DNA thus purified was digested with SacII and BamHI, and deletion was made by intermittent ExoIII excision reaction using Erase-a-Base system (Promega, USA). The deleted DNAs were self-ligated by $T_4$ DNA ligase and introduced into competent E. coli XL1-Blue cell treated with $CaCl_2$ solution. Deletion mutants were employed to determine DNA sequence.

After single strand preparation by alkali denaturation method, the full DNA sequence of PAP genome was determined by SEQUENASE VERSION 2.0(United States Biochemical, USA) employing primer such as $T_7$ promoter primer or universal reverse primer. FIG. 1 is the full nucleotide sequence(SEQ ID NO:1) of the PAP gene and amino acid sequence(SEQ ID NO:2) translated therefrom. As disclosed in FIG. 1, the PAP cDNA consists of an open reading frame of 1195 bp; and PAP cDNA codes 313 of amino acid residues, 22 residues of which function as signal peptide. Polyadenylation signal(AATAAA) which is ubiquitous in mRNA of most plants and animals, appears to be located 17 bp upstream from the polyadenylation site. An amino acid sequence prevalent in ribosome-inactivating proteins(RIP: Abrin A, Luffin-a, MAP, Ricin A., Trichosanthin and SO6) was also found in PAP gene (Ile-Gln-Met-Val-Ser-Glu-Ala-Ala-Arg-Phe-Lys-Tyr-Ile)(SEQ ID NO:3), which is determined to be the active site of RIP.

EXAMPLE 3

Preparation of Expression Vector pJRM100

To express the isolated PAP gene under the control of CaMV 35S promoter, the 5' site of the PAP gene was deleted upto the site of translational initiation(ATG) as follows: PAP gene was double digested with SacII and BamHI; and, ExoIII treatment at 30° C. for 10 sec followed. About 30 bp was deleted by $S_1$ nuclease treatment, ligated to BamHI linker by $T_4$ DNA ligase. DNAs manipulated at the 5' site were selected and employed for further experiment. Then, said 5' site manipulated DNA was digested with HindIII, treated with Klenow's fragment and ligated to BamHI linker to link the 3' site of the PAP gene with nopaline synthase terminator("Nos terminator"). The DNA fragment containing 5' and 3' sites manipulated as above was subject to BamHI digestion, then about 1.0 kb BamHI fragment of PAP gene was isolated by unidirectional electroelution on agarose gel.

Figure 2B:
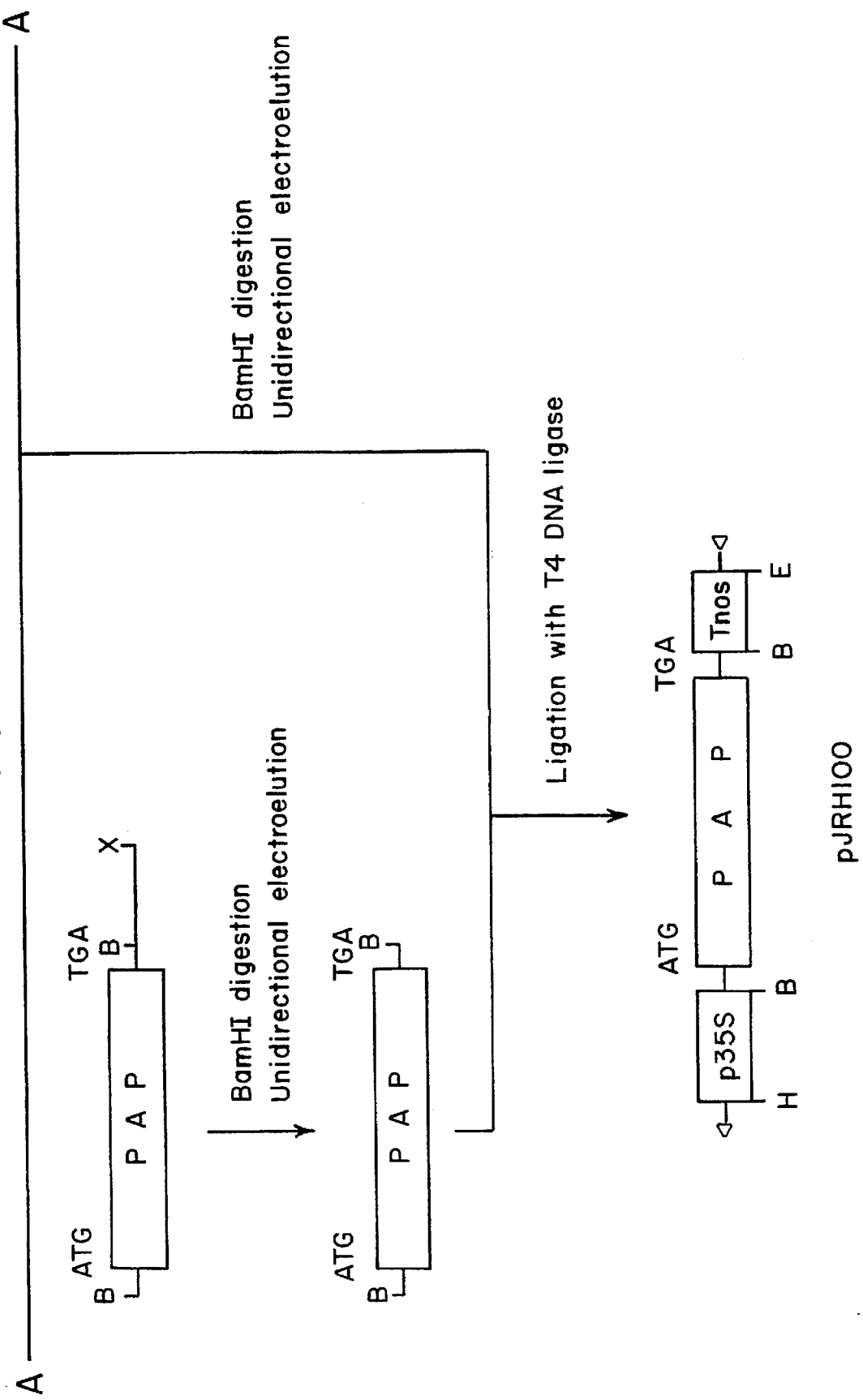
Figure 3:
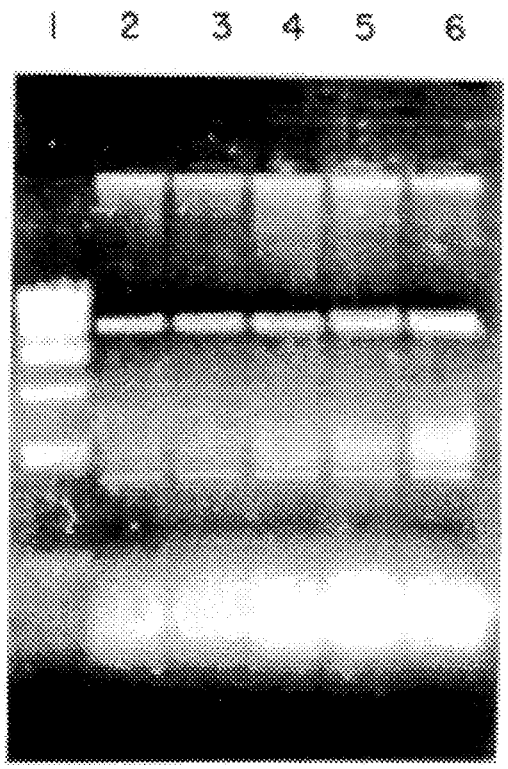
FIG. 3 is a photograph showing agarose gel electrophoresis pattern of expression vector pJRM100 digested with restriction enzymes.

To insert 1.0 kb BamHI fragment of PAP gene into binary vector pBI121(Clonetech, Lot #6019-2, USA), SstI restriction site near the Nos terminator was substituted with BamHI restriction site as follows: pBI121 was treated with SstI, and Klenow's fragment treatment and ligation with BamHI linker were carried out in a serial manner. Selection of DNA of interest followed and subject to BamHI digestion. Then, about 11.06 kb of BamHI fragment was isolated by unidirectional electroelution on agarose gel.

pJRM100 was prepared by ligating 11.06 kb BamHI fragment of pBI121 with 1.0 kb BamHI fragment of PAP gene by $T_4$ DNA ligase. Example 3 is schematically illustrated in FIG. 2. FIG. 3 shows an agarose gel electrophoresis pattern of pJRM100 digested with restriction enzymes. In FIG. 3, lane 1 is λDNA digested with HindIII as molecular marker; and, lanes 2, 3, 4, 5 and 6 are expression vector pJRM100 digested with HindIII and XhoI.

EXAMPLE 4

Preparation of Agrobacterium Mediator for Plant Cell Transformation

Freeze-thawing method was employed to transform *Agrobacterium tumefaciens* LBA 4404 with pJRM100 prepared in Example 3, where PAP gene expression is controlled under a CaMV promoter. To select *Agrobacterium tumefaciens* LBA 4404 transformed with pJRM100, plasmid DNA was isolated from the Agrobacterium by a quick-screening method(see: Stanton B. G. et al., Plant Molecular Biology Manual, Kluwer, Academic Publishers(1988)) and digested with BamHI. *Agrobacterium tumefaciens* LBA 4404 transformed with pJRM100 was deposited with the Korean Collection for Type Culture(KCTC) on Aug. 7, 1992 as deposition No. KCTC 0052BP.

*Agrobacterium tumefaciens* LBA 4404 transformed with pJRM100(KCTC 0052BP), a mediator for plant cell transformation, was incubated in a shaking incubator at 28° C., 200 rpm for 18 hrs. After incubation, said cells were harvested, emulsified with MS medium to the concentration of 1 to $2 \times 10^3$ cells/ml and employed for plant transformation.

EXAMPLE 5

Preparation of Transgenic Tobacco Plant

EXAMPLE 5-1

Transformation of Tobacco Cell

Tobacco plants, *Nicotiana tabacum* NC2326 and *Nicotiana tabacum xanthi*, were prepared as follows: tobacco seed was treated with 70(v/v)% ethanol for 5 min and 50(v/v)% bleaching agent for 20 min, respectively, washed with distilled water 3 times and incubated on MS basic medium; and, leaves grown for 1 month in incubator were chopped up in a proper size and employed as host plant cell for transformation.

Tobacco leaf discs were co-cultivated with the Agrobacterium cell harboring pJRM100 for 30 min and the transformants were incubated on MS medium comprising 1.0 mg/l BAP(benzylamino purine) and 0.1 mg/l NAA(α-naphthalene acetic acid) at 26° C. for 48 hrs under dark condition.

Figure 4A:
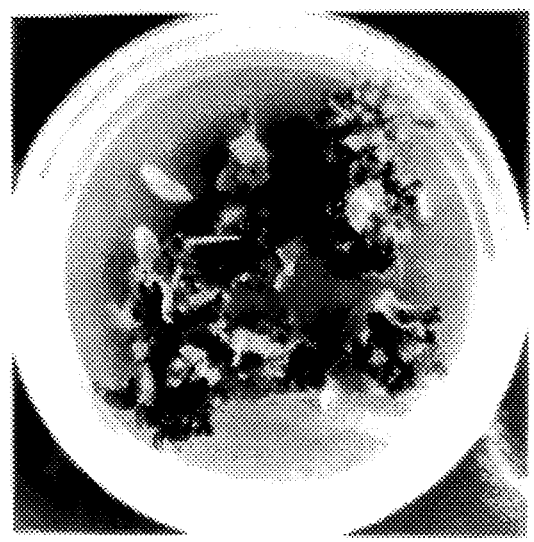
FIG. 4(A) is a photograph showing shoot induction from the transgenic tobacco cell transformed with pJRM100.
Figure 4B:
FIG. 4(B) is a photograph showing root generation from the shoot.
Figure 4C:
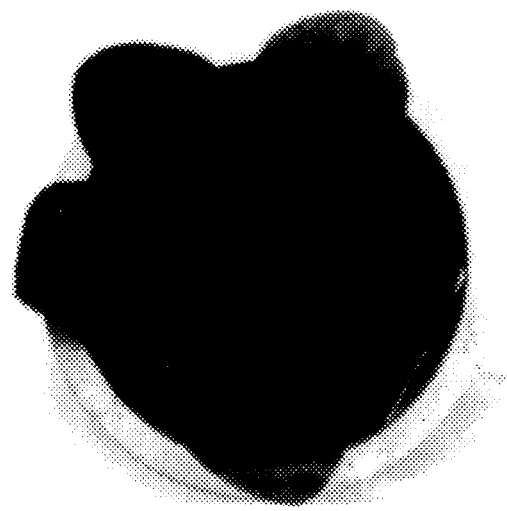
FIG. 4(C) is a photograph showing transgenic tobacco plant adapted in the soil pot.

Shoots were induced from the leaf discs by incubation on MS selective medium comprising 1.0 mg/l BAP, 100 mg/l kanamycin and 500 mg/l carbenicillin with 16 hrs light (about 3000 lux) and 8 hrs dark cycle(see: FIG. 4(A)). The induced shoots were subject to root generation by incubation on MS basic medium containing 100 mg/l kanamycin and 250 mg/l carbenicillin(see: FIG. 4(B)) and the rooted tobacco plants were transferred to the soil pots and adapted (see: FIG. 4(C)) for later use.

EXAMPLE 5-2

Detection of PAP Gene in Transgenic Tobacco Plant

To determine proper insertion of PAP gene into tobacco DNA, Southern blot analysis was carried out. Total DNA was isolated from transgenic tobacco, digested with BamHI, and electrophoresed on 0.8%(v/w) agarose gel. The fractionated DNAs were transferred to Hybond-N+; and, hybridization was followed by employing 1.0 kb BamHI fragment of PAP gene prepared in Example 3 as a probe. In this connection, probe was prepared by nick translation kit (Promega, USA) and labelled with $\alpha$-$^{32}$p dATP.

Figure 5:
FIG. 5 is a photograph showing the Southern blot analysis of DNA isolated from transgenic tobacco plant.

FIG. 5 is a photograph showing the Southern blot analysis of DNA isolated from the transgenic tobacco plants. In FIG. 5, lane 1 is DNA from non-transgenic tobacco; lanes 2, 3 and 4 are DNA from transgenic tobacco; and, lane 5 is pJRM100. As can be seen in FIG. 5, all of lanes 2, 3, 4 and 5 show bands of same position, while no band is showed in non-transgenic tobacco of lane 1. Accordingly, it is clearly demonstrated that PAP gene was properly inserted into the genome of transgenic tobacco plants.

EXAMPLE 5-3

Determination of PAP Gene Transcription in Transgenic Tobacco Plant

Figure 6:
FIG. 6 is a photograph showing the Northern blot analysis of RNA isolated from transgenic tobacco plant.

To determine transcription level in the transgenic tobacco plant, total cellular RNA was isolated, electrophoresed on 1(v/w)% agarose gel, transferred to Hybond-N+; and, hybridization was carried out by employing the probe used in the Southern blot analysis. FIG. 6 is a photograph showing the Northern blot analysis of RNA isolated from transgenic tobacco plant. In FIG. 6, lane 1 is RNA from non-transgenic tobacco; and, lane 2 is RNA from transgenic tobacco. As can be seen in FIG. 6, lane 1 shows no band, while a band is showed in transgenic tobacco of lane 2. Accordingly, it is concluded that PAP gene inserted into the genome of transgenic tobacco was transcribed in a proper manner.

EXAMPLE 5-4

Determination of PAP Expression in Transgenic Tobacco Plant

To determine PAP expression in transgenic tobacco plant, immunodiffusion assay and Western blot analysis were employed, respectively.

Figure 7:
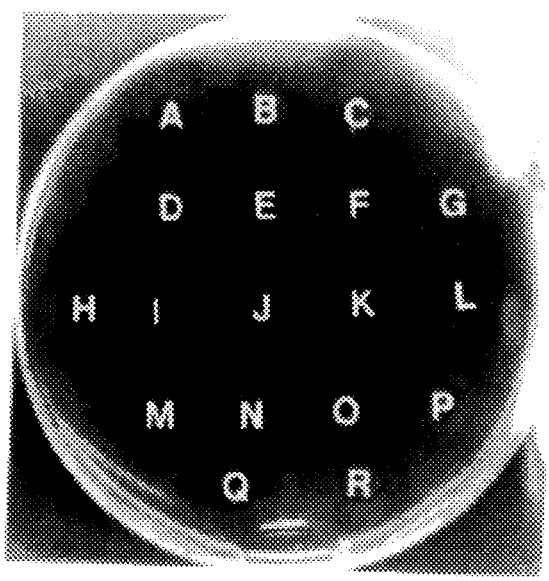
FIG. 7 is a photograph showing the immunodiffusion assay of PAP expressed in transgenic tobacco plant.

The immunodiffusion assay was carried out as follows: 0.8(v/w)% agar and 5 μg/ml anti-PAP antibody prepared in Example 1 were poured on petri dish coated with 1(v/w)% agar. Pores for sample loading were installed on solid agar plate. Then, total proteins were isolated from transgenic tobacco and were loaded in pores of agar plate prepared as above. Agar plate was incubated for 48 hrs, stained with dye solution, destained with destaining solution; and, precipitate produced was determined. FIG. 7 illustrates the result of immunodiffusion assay. In FIG. 7, total proteins of *Phytolacca americana* L. and non-transgenic tobacco are contained in the pores C and B, respectively; and, other pores contains total proteins isolated from transgenic tobacco. As can be seen in FIG. 7, all the pores except B show halo rings around the pores, which mean PAP:anti-PAP antibody reaction. Accordingly, it is clearly demonstrated that PAP was expressed in transgenic tobacco plant.

Figure 8:
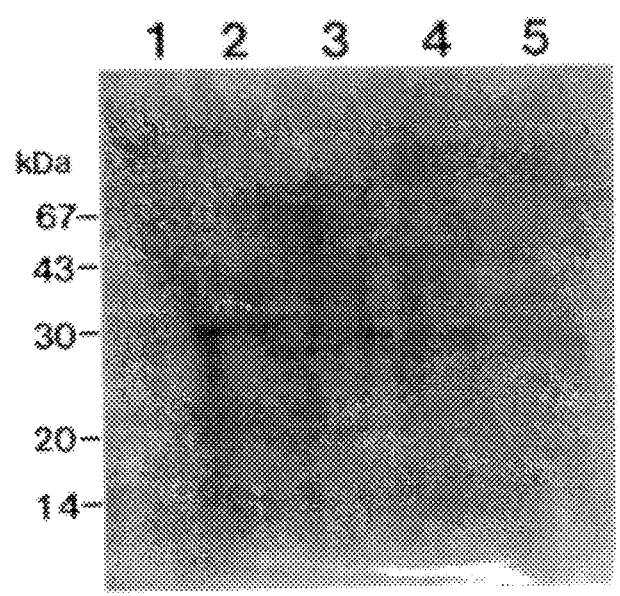
FIG. 8 is a photograph showing the Western blot analysis of total proteins isolated from transgenic tobacco plant.

Western blot analysis was also performed with total proteins isolated from transgenic tobacco according to Sambrook et al.'s method(see: Sambrook, J. et al., Molecular cloning: A Laboratory Manual, Cold Spring Harbor Laboratory, Cold Spring Harbor, N.Y., 1989): total proteins were extracted from the leaves of transgenic tobacco, separated in a 15% SDS-polyacrylamide gel and transferred onto Hybond-C extra membrane (Amersham, UK). The membrane was blocked with PBS solution containing 0.1% Tween 20 and 2% BSA. After washing twice with washing buffer containing 0.1% Tween 20 for 5 min, the membrane was treated with 2 g/ml rabbit anti-PAP antibody for 1 hr at room temperature, washed twice with washing buffer(PBS solution containing 0.1% Tween 20) and incubated with rabbit peroxidase-conjugated second antibody (Pierce, USA) for 1 hr at room temperature. After washing twice with washing buffer, the membrane was stained with 4-chloro-1-naphtol(see: FIG. 8). In FIG. 8, lane 1 is total proteins of non-transgenic tobacco plant; and, lanes 2, 3, 4 and 5 are total proteins of transgenic tobacco plants. As can be seen in FIG. 8, about 30 kDa protein of mature PAP is detected in all the transgenic tobacco plants of lanes 2–5, while it is undetectable in a non-transgenic tobacco plant of lane 1.

As demonstrated in the results of immunodiffusion assay and Western blot analysis, it is clearly determined that the PAP gene was expressed in transgenic tobacco plant.

EXAMPLE 5-5

Determination of Viral Resistance of Transgenic Tobacco Plant

Lyophilized TMV-infected tissue(ATCC PV226) obtained from ATCC was chopped up, dissolved in phosphate buffer solution and centrifuged. Supernatant thus obtained was formulated for virus innoculation; and applied to leaves of the test plants of 4 to 6 leaves stage. After 7 and 25 days from the virus innoculation, local lesion assay was carried out in a growth chamber(see: FIGS. 9(A), 9(B), 10(A) and 10(B)).

Figure 9A:
FIG. 9(A) is a photograph showing the result of local lesion assay of transgenic tobacco plant after 7 days from the virus innoculation.
Figure 9B:
FIG. 9(B) is a photograph showing the result of local lesion assay of non-transgenic tobacco plant after 7 days from the virus innoculation.
Figure 10A:
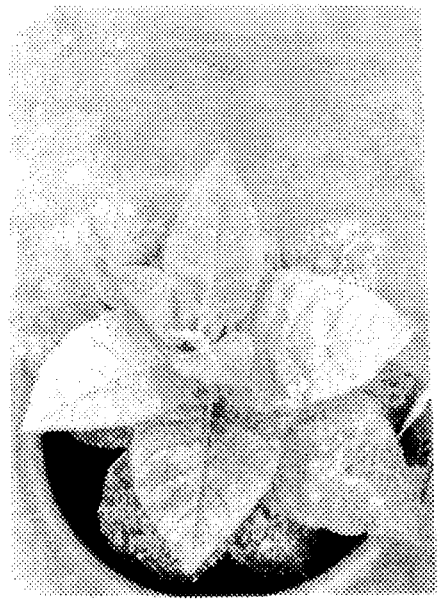
FIG. 10(A) is a photograph showing the result of local lesion assay of non-transgenic tobacco after 25 days from the virus innoculation.
Figure 10B:
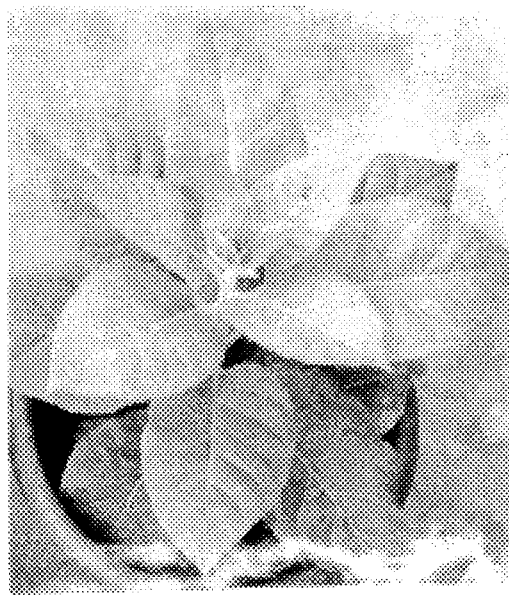
FIG. 10(B) is a photograph showing the result of local lesion assay of transgenic tobacco after 25 days from the virus innoculation.

FIGS. 9(A) and 9(B) are photographs showing the leaves of transgenic and non-transgenic tobacco plants after 7 days from the virus innoculation, respectively. As can be seen in FIGS. 9(A) and 9(B), no local lesions are detected in transgenic tobacco, while local lesions are clearly observed in non-transgenic tobacco. FIGS. 10(A) and 10(B) are photographs of non-transgenic and transgenic tobacco plants after 25 days from the virus innoculation, respectively. As can be seen in FIGS. 10(A) and 10(B), local lesions are not detected in transgenic tobacco and its growth is normal, while local lesions are observed in non-transgenic tobacco and its growth is retarded. As clearly illustrated and demonstrated as aboves, it is naturally concluded that expression of the PAP gene repeatedly confers resistance to TMV on transgenic tobacco plants.

EXAMPLE 6

Preparation of Transgenic Potato Plant

EXAMPLE 6-1

Transformation of Potato Cell

Potato tubers were surface-sterilized and were cut into pieces of 1 cm in length. The tuber pieces were co-cultivated with the Agrobacterium cell harboring pJRM100 for 30 min and incubated in MS medium containing 1.0 mg/l zeatin and 0.5 mg/l IAA (3-β-indoleacrylic acid) at 20° C. for 48 hrs under dark condition. Shoots were induced from the tuber pieces on the MS medium containing 1.0 mg/l zeatin, 0.5 mg/l IAA, 100 mg/l kanamycin and 500 mg/l carbenicillin at 25 days after incubation and subject to generation of root on MS medium containing 250 mg/l carbenicillin and 100 mg/l kanamycin. Almost all of the shoots generated roots normally, and regenerated potato plants were transferred to soil pot and adapted for later use. Three of transgenic potato cell lines showed root generation were named with lines '1021', '1022' and '1023', respectively. Transgenic potato cell lines grown upto 15 cm in length on soil pots were employed for further experiments.

EXAMPLE 6-2

Detection of PAP Gene in Transgenic Potato Plant

Figures 11, 12:
FIG. 11 is a photograph showing the Southern blot analysis of DNA isolated from transgenic potato plant.
FIG. 12 is a photograph showing the Western blot analysis of total proteins isolated from transgenic potato plant.

To determine proper insertion of PAP gene into potato DNA, Southern blot analysis was carried out. Genomic DNA was purified from the transgenic potato and amplified by polymerase chain reaction. 5'-CCAAGCTTGTGAATACAAT CATCTAC-3' (SEQ ID NO:4) and 5'-GGAAGCTTTGATCAGAATCCTTCAAA-3' (SEQ ID NO:5) were employed as the N-terminal and the C-terminal primers, respectively. The amplified DNAs were subject to Southern hybridization using the probe of 0.6 kb EcoRI fragment of PAP cDNA labelled with the DIG-Labelling and Detection Kit(Boehringer Mannheim, Germany) (see: FIG. 11). In FIG. 11, lane 1 is DNA from non-transgenic potato plant; lanes 2, 3, 4 and 5 are DNAs from transgenic potato plants; and, lane 6 is DNA amplified from PAP cDNA clone. As can be seen in FIG. 11, DNAs amplified from genomic DNAs of all the transgenic potato plants of lanes 2–5 were hybridized with the probe, while amplified DNA of a non-transgenic potato plant was not. Accordingly, it is clearly demonstrated that PAP gene was properly integrated into the genome of transgenic potato plant.

EXAMPLE 6-3

Determination of PAP Expression in Transgenic Potato Plant

To investigate whether the transferred PAP gene is expressed in the transgenic potato plant, total proteins extracted from leaves of the transgenic potato were subject to Western blot analysis as described in Example 5-4(see: FIG. 12). In FIG. 12, lane 1 is total proteins of non-transgenic potato plant; and, lanes 2, 3, 4 and 5 are total proteins of transgenic potato plants. As can be seen in FIG. 12, about 30kDa protein was detected in all the transgenic tobacco plants of lanes 2–5, while undetectable in a non-transgenic tobacco plant of lane 1. Accordingly, it could be concluded that the transferred PAP gene was expressed in transgenic potato plant.

EXAMPLE 6-4

Determination of Viral Resistance of Transgenic Potato Plant

Transgenic potato cell lines 1021, 1022 and 1023 and nontransgenic potato were inoculated with PVX(potato virus X), PVY(potato virus Y) and PLRV(potato leafroll virus), respectively. PVX and PVY were inoculated on leaves after wounding with cotton wool treated with carborundum. PLRV was inoculated by mediation of 10 aphids (Myzus persicae) feeded for 3 days on potato leaves infected with PLRV, after which aphids were killed with insecticide.

The inoculated leaves were removed at 15, 30 and 45 days after inoculation and subject to ELISA assay to determine titer of each virus(see: Clark, M. F. et al., J. Gen. Virol., 34:475–483(1977)). Microtiter plates with 98 wells were coated with 200 µl(per each well) of 1000-fold diluted polyclonal antibodies (BIOREBA AG Co., Germany) against each virus at 37° C. for 4 hrs. The plates were washed with PBS solution containing 0.05% Tween 20 for 3 times, reacted with 20 µl of leaf extract in PBS solution (1:20=leaf extract:PBS solution, v/v) at 6 ° C. for 16 hrs and then with 200 µl of 1000-fold diluted polyclonal alkaline phosphatase-conjugated IgG(BIOREBA AG Co., Germany). After washing with PBS solution for 3 times, phosphatase activity was determined with 200 µl of p-nitrophenyl-phosphate(1 mg/ml) to produce p-nitrophenol whose absorbance is measured at 405 nm.

Figure 13:
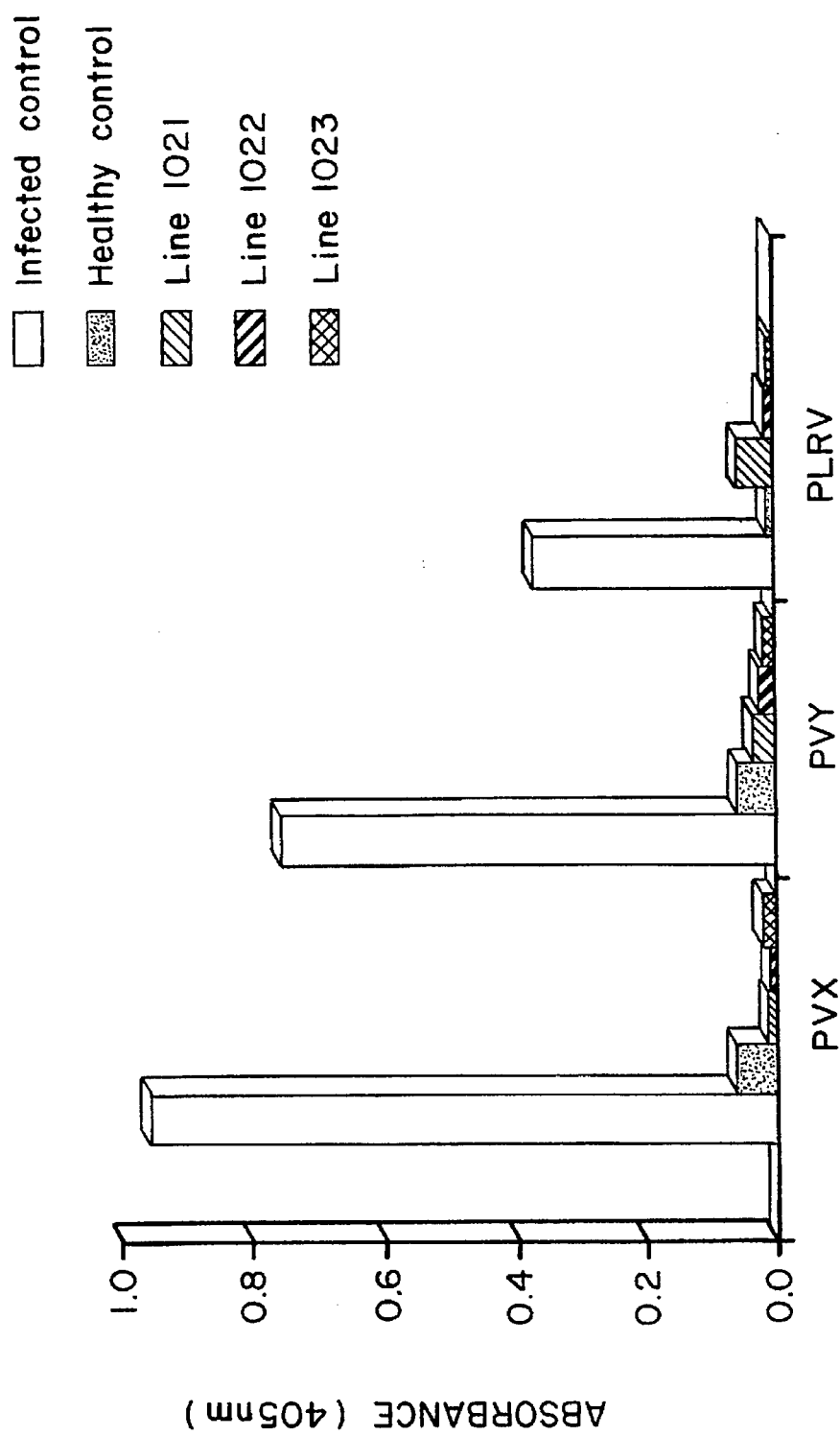
FIG. 13 is a graph showing broad-spectrum of viral resistance in the transgenic potato plant.

FIG. 13 is a graph showing the results of ELISA at 30 days after inoculation. As can be seen in FIG. 13, transgenic plant lines 1021, 1022 and 1023 revealed much lower levels of PVX and PVY than infected control plants, and showed lower level than even healthy control plants(non-infected); and, the level of PLRV particles was also lower in transgenic plants than infected plants.

Figure 14A:
FIG. 14(A) is a photograph showing no viral resistance for PVY(potato virus Y) in a non-transgenic potato plant; and, FIG. 14(B) is a photograph showing viral resistance for PVY in transgenic potato plant.
Figure 14B:
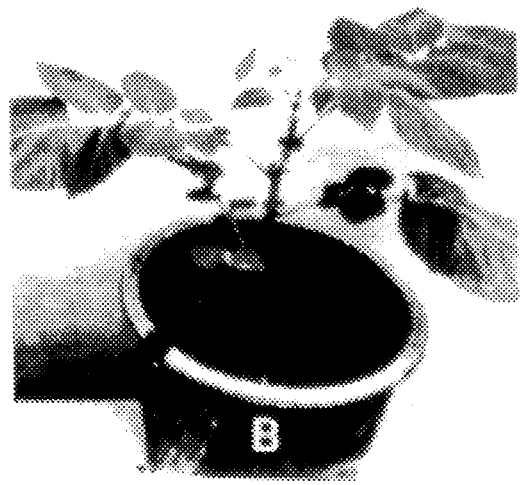

On the other hand, non-transgenic and transgenic potato plants were infected with PVY, respectively; and symptom development on infected plants were observed with the naked eyes after 45 days from the virus inoculation. FIG. 14(A) shows symptom of necrosis throughout veins in non-transgenic potato plant, while FIG. 14(B) shows viral resistance in transgenic potato plant. Accordingly, it is clearly demonstrated that the transgenic potato plants transformed with the expression vector of the invention were continuously resistant to viral infection.

As clearly illustrated and demonstrated above, the present invention provides a process for preparing transgenic plants transformed with a recombinant vector for PAP. The transgenic plants of the invention were properly transformed with the recombinant vector of the invention; PAP was expressed from the transgenic plants in a successful manner; and, virus proliferation was efficiently inhibited by the expressed PAP in the transgenic plants.

---

What is claimed is:

1. *Agrobacterium tumefaciens* LBA 4404 transformed with recombinant DNA pJRM100 (KCTC 0052BP), which is capable of expressing *Phytolacca americana* antiviral protein.

2. A process for preparing virus-resistant transgenic plant which comprises the step of transforming a plant with *Agrobacterium tumefaciens* that has been transformed with the recombinant DNA pJRM100, which is capable of expressing *Phytolacca americana* antiviral protein.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1195 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Phytolacca americana
        ( F ) TISSUE TYPE: Leaf ( x i ) SEQUENCE DESCRIPTION: SEQ ID NO:1:

-continued

```
GAGGAGAGAG AACTAGTTAG TAGGAAGGGA AGATGAAGTC GATGCTTGTG GTGACAATAT    60
CAATATGGCT CATTCTTGCA CCAACTTCAA CTTGGGCTGT GAATACAATC ATCTACAATG   120
TTGGAAGTAC CACCATTAGC AAATACGCCA CTTTTCTGAA TGATCTTCGT AATGAAGCGA   180
AAGATCCAAG TTTAAAATGC TATGGAATAC CAATGCTGCC AATACAAAT  ACAAATCCAA   240
AGTACGTGTT GGTTGAGCTC CAAGGTTCAA ATAAAAAAC  CATCACACTA ATGCTGAGAC   300
GAAACAATTT GTATGTGATG GGTTATTCTG ATCCCTTTGA AACCAATAAA TGTCGTTACC   360
ATATCTTTAA TGATATCTCA GGTACTGAAC GCCAAGATGT AGAGACTACT CTTTGCCCAA   420
ATGCCAATTC TCGTGTTAGT AAAAACATAA ACTTTGATAG TCGATATCCA ACATTGGAAT   480
CAAAGCGGG  AGTAAAATCA AGAAGTCAAG TCCAACTGGG AATTCAAATA CTCGACAGTA   540
ATATTGGAAA GATTTCTGGA GTGATGTCAT TCACTGAGAA AACCGAAGCC GAATTCCTAT   600
TGGTAGCCAT ACAAATGGTA TCAGAGGCAG CAAGATTCAA GTACATAGAG AATCAGGTGA   660
AAACTAATTT TAACAGAGCA TTCAACCCTA ATCCCAAAGT ACTTAATTTG CAAGAGACAT   720
GGGGTAAGAT TCAACAGCA  ATTCATGATG CCAAGAATGG AGTTTTACCC AAACCTCTCG   780
AGCTAGTGGA TGCCAGTGGT GCCAAGTGGA TAGTGTTGAG AGTGGATGAA ATCAAGCCTG   840
ATGTAGCACT CTTAAACTAC GTTGGTGGGA GCTGTCAGAC AACTTATAAC CAAAATGCCA   900
TGTTTCCTCA ACTTATAATG TCTACTTATT ATAATTACAT GGTTAATCTT GGTGATCTAT   960
TTGAAGGATT CTGATCATAA ACTTAATAAG GAGTATATAT ATATTACTCC AACTATATTA  1020
TAAAGCTTAA ATAAGAGGCC GTGTTAATTA GTACTTGTTG CCTTTTGCTT TATGGTGTTG  1080
TTTATTATGC CTTGTATGCT TGTAATATTA TCTAGAGAAC AAGATGTACT GTGTAATAGT  1140
CTTGTTTGAA ATAAAACTTC CAATTATGAT GCAAAAAAAA AAAAAAAAA  AAAAA       1195
```

( 2 ) INFORMATION FOR SEQ ID NO:2:

( i ) SEQUENCE CHARACTERISTICS:
        ( A ) LENGTH: 313 amino acids
        ( B ) TYPE: amino acid
        ( C ) STRANDEDNESS:
        ( D ) TOPOLOGY: linear ( i i ) MOLECULE TYPE: protein ( v ) FRAGMENT TYPE: N-terminal ( v i ) ORIGINAL SOURCE:
        ( A ) ORGANISM: Phytolacca americana
        ( F ) TISSUE TYPE: Leaf ( x i ) SEQUENCE DESCRIPTION: SEQ ID NO:2:

```
Met Lys Ser Met Leu Val Val Thr Ile Ser Ile Trp Leu Ile Leu Ala
 1               5                  10                  15

Pro Thr Ser Thr Trp Ala Val Asn Thr Ile Ile Tyr Asn Val Gly Ser
             20                  25                  30

Thr Thr Ile Ser Lys Tyr Ala Thr Phe Leu Asn Asp Leu Arg Asn Glu
         35                  40                  45

Ala Lys Asp Pro Ser Leu Lys Cys Tyr Gly Ile Pro Met Leu Pro Asn
     50                  55                  60

Thr Asn Thr Asn Pro Lys Tyr Val Leu Val Glu Leu Gln Gly Ser Asn
 65                  70                  75                  80

Lys Lys Thr Ile Thr Leu Met Leu Arg Arg Asn Asn Leu Tyr Val Met
                 85                  90                  95

Gly Tyr Ser Asp Pro Phe Glu Thr Asn Lys Cys Arg Tyr His Ile Phe
            100                 105                 110
```

```
Asn Asp Ile Ser Gly Thr Glu Arg Gln Asp Val Glu Thr Thr Leu Cys
    115             120             125
Pro Asn Ala Asn Ser Arg Val Ser Lys Asn Ile Asn Phe Asp Ser Arg
    130             135             140
Tyr Pro Thr Leu Glu Ser Lys Ala Gly Val Lys Ser Arg Ser Gln Val
145             150             155                             160
Gln Leu Gly Ile Gln Ile Leu Asp Ser Asn Ile Gly Lys Ile Ser Gly
                165             170             175
Val Met Ser Phe Thr Glu Lys Thr Glu Ala Glu Phe Leu Leu Val Ala
            180             185             190
Ile Gln Met Val Ser Glu Ala Ala Arg Phe Lys Tyr Ile Glu Asn Gln
        195             200             205
Val Lys Thr Asn Phe Asn Arg Ala Phe Asn Pro Asn Pro Lys Val Leu
    210             215             220
Asn Leu Gln Glu Thr Trp Gly Lys Ile Ser Thr Ala Ile His Asp Ala
225             230             235                             240
Lys Asn Gly Val Leu Pro Lys Pro Leu Glu Leu Val Asp Ala Ser Gly
                245             250             255
Ala Lys Trp Ile Val Leu Arg Val Asp Glu Ile Lys Pro Asp Val Ala
            260             265             270
Leu Leu Asn Tyr Val Gly Gly Ser Cys Gln Thr Thr Tyr Asn Gln Asn
        275             280             285
Ala Met Phe Pro Gln Leu Ile Met Ser Thr Tyr Tyr Asn Tyr Met Val
    290             295             300
Asn Leu Gly Asp Leu Phe Glu Gly Phe
305             310
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: protein ( v ) FRAGMENT TYPE: internal ( v i ) ORIGINAL SOURCE:
        ( A ) ORGANISM: Phytolacca americana
        ( F ) TISSUE TYPE: Leaf ( x i ) SEQUENCE DESCRIPTION: SEQ ID NO:3:

```
Ile Gln Met Val Ser Glu Ala Arg Phe Lys Tyr Ile
1               5                   10
```

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCAAGCTTGT GAATACAATC ATCTAC      26

( 2 ) INFORMATION FOR SEQ ID NO:5:

-continued

```
( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

GGAAGCTTTG ATCAGAATCC TTCAAA        26
```